(12) United States Patent
Nyberg, II et al.

(10) Patent No.: US 9,393,428 B2
(45) Date of Patent: Jul. 19, 2016

(54) IMPLANTABLE ANTENNA ASSEMBLIES

(75) Inventors: David Andre Nyberg, II, Frazier Park, CA (US); Andreas B. Brehm, Adelsdorf (DE); Thomas Mehl, Santa Clarita, CA (US)

(73) Assignee: ADVANCED BIONICS AG, Staefa (CH)

( * ) Notice: Subject to any disclaimer, the term of this patent is extended or adjusted under 35 U.S.C. 154(b) by 0 days.

(21) Appl. No.: 14/384,339

(22) PCT Filed: Mar. 29, 2012

(86) PCT No.: PCT/US2012/031238
§ 371 (c)(1),
(2), (4) Date: Sep. 10, 2014

(87) PCT Pub. No.: WO2013/147799
PCT Pub. Date: Oct. 3, 2013

(65) Prior Publication Data
US 2015/0025613 A1 Jan. 22, 2015

(51) Int. Cl.
*A61N 1/00* (2006.01)
*A61N 1/372* (2006.01)
*H01Q 1/27* (2006.01)
(Continued)

(52) U.S. Cl.
CPC ............ *A61N 1/37229* (2013.01); *H01Q 1/273* (2013.01); *H01Q 9/27* (2013.01); *A61N 1/375* (2013.01); *Y10T 29/49018* (2015.01)

(58) Field of Classification Search
CPC ..... H05K 3/46; H05K 3/4061; H05K 3/4069; H05K 9/0052; H05K 1/112; H05K 1/11; H05K 1/118; Y10T 29/49016; Y10T 29/49018
See application file for complete search history.

(56) References Cited

U.S. PATENT DOCUMENTS

| 4,026,276 A | 5/1977 | Chubbuck |
| 6,275,737 B1 * | 8/2001 | Mann ...................... A61N 1/08 607/61 |
| 6,463,336 B1 | 10/2002 | Mawhinney |

(Continued)

FOREIGN PATENT DOCUMENTS

| EP | 1944827 A2 | 7/2008 |
| EP | 1389143 B1 | 4/2013 |

(Continued)

OTHER PUBLICATIONS

Urbani F et al: "Low Cost Compact Active Integrated Antenna with a Reactive Impedance Surface", Wireless Communications and Applied Computational Electromagnetics, International Conference on Honolulu, Apr. 2005 (Apr. 3, 2005), pp. 257-260, abstract only.

(Continued)

*Primary Examiner* — Robert N Wieland
(74) *Attorney, Agent, or Firm* — Fabian VanCott; Steven L. Nichols

(57) ABSTRACT

An implantable antenna assembly includes a multilayer flexible printed circuit board comprising a first flexible substrate, second flexible substrate, and third flexible substrate. An inductor coil is formed by electrically conductive traces disposed on the first flexible substrate. A shield is formed by electrically conductive traces disposed on the second flexible substrate and third flexible substrate, the shield surrounding the inductor coil. A method for forming an implantable antenna assembly is also provided.

27 Claims, 11 Drawing Sheets

(51) Int. Cl.
*H01Q 9/27* (2006.01)
*A61N 1/375* (2006.01)

(56) References Cited

U.S. PATENT DOCUMENTS

| | | | |
|---|---|---|---|
| 7,260,435 B2 | 8/2007 | Ibrahim | |
| 7,800,078 B2 | 9/2010 | Colvin, Jr. et al. | |
| 8,126,563 B2 | 2/2012 | Ibrahim | |
| 8,929,999 B2* | 1/2015 | Maschiach | A61N 1/0551 607/134 |
| 8,989,868 B2* | 3/2015 | Mashiach | A61N 1/0551 600/529 |
| 2004/0044382 A1 | 3/2004 | Ibrahim | |
| 2005/0182389 A1 | 8/2005 | Laporte et al. | |
| 2005/0205291 A1* | 9/2005 | Yamashita | H05K 3/20 174/254 |
| 2006/0227060 A1* | 10/2006 | Hess | A61N 1/37229 343/788 |
| 2007/0100385 A1 | 5/2007 | Rawat et al. | |
| 2007/0229279 A1 | 10/2007 | Yamazaki et al. | |
| 2008/0046034 A1 | 2/2008 | Ibrahim | |
| 2008/0177353 A1 | 7/2008 | Hirota et al. | |
| 2008/0300658 A1 | 12/2008 | Meskens | |
| 2008/0315311 A1 | 12/2008 | Okamoto | |
| 2009/0065588 A1 | 3/2009 | Aoki et al. | |
| 2009/0222066 A1 | 9/2009 | Chen et al. | |
| 2010/0114245 A1 | 5/2010 | Yamamoto et al. | |
| 2011/0009925 A1 | 1/2011 | Leigh et al. | |
| 2011/0221561 A1* | 9/2011 | Mori | H01F 17/0013 336/200 |
| 2012/0089202 A1 | 4/2012 | Staller | |

FOREIGN PATENT DOCUMENTS

| | | |
|---|---|---|
| WO | 2009124174 A2 | 10/2009 |
| WO | 2010051249 | 5/2010 |
| WO | 2012011065 | 1/2012 |
| WO | 2012047967 | 4/2012 |

OTHER PUBLICATIONS

Romulo F Jimenez Broas et al: "A High-Impedance Ground Plane Applied to a Cellphone Handset Geometry", IEEE Transactions on Microwave Theory and Techniques, IEEE Service Center, Piscataway, NJ, US, vol. 49, No. 7, Jul. 1, 2001, XP011038350, ISSN: 0018-9480.

Mosallaei H et al: "Antenna Miniaturization and Bandwidth Enhancement Using a Reactive Impedance Substrate", IEEE Transactions on Antennas and Propagation, IEEE Service Center, Piscataway, NJ, US, Vol. vol. 52, No. 9, Sep. 1, 2004, pp. 2403-2414, XP011118434, ISSN: 0018-926X.

* cited by examiner

Fig. 9A     Fig. 9B

IMPLANTABLE ANTENNA ASSEMBLIES

BACKGROUND

Implantable antenna assemblies can be used for wireless transmission of signals and power to an implanted medical device. For example, a cochlear implant system includes an external portion and an implanted portion. The external portion communicates signals and power to the implanted portion through the skin of the patient. The implanted portion includes an antenna assembly that receives the signals and power.

BRIEF DESCRIPTION OF THE DRAWINGS

The accompanying drawings illustrate various examples of the principles described herein and are a part of the specification. The illustrated examples are merely examples and do not limit the scope of the claims.

FIGS. 9A-9C show an embodiment with a cage that retains a magnet, according to one example of principles described herein.

Throughout the drawings, identical reference numbers designate similar, but not necessarily identical, elements.

DETAILED DESCRIPTION

A variety of implanted devices, such as pacemakers and cochlear implants, use an implanted antenna assembly to receive power and electrical signals through the patient's skin. The implantable antenna assembly is designed to meet specific criteria for biocompatibility, lifetime, and transmission efficiency. For example, a cochlear implant system typically comprises both an external unit that receives and processes ambient sound waves and an implanted processor/electrode array that receives data and power from the external unit via an implanted antenna. The implanted processor/electrode array uses this data and power to directly stimulate the auditory nerve.

The antenna assembly for a typical cochlear implant includes an inductor made from a metal strand such as gold or platinum that is wound in one or several loops. An electromagnetic shield is formed around the inductor to reduce noise and undesirable alteration of the characteristics of the inductor by external objects. The inductor and electromagnetic shield are embedded in silicone. The ends of the strand are connected to the electronics in the implanted processor of the implant. The antenna assembly receives the information and energy sent through the skin flap by a headpiece. The antenna assembly designed to be flexible so that it can adjust to the shape of the skull.

These antenna assemblies for cochlear implants are manufactured by highly skilled technicians in a largely manual process. This results in the antenna assemblies being very costly and prone to some amount of deviation in electrical and mechanical properties. The deviation in electrical properties can result in antennas assemblies built by the same process having different transmission characteristics. Each antenna assembly is individually calibrated and tuned so that the antenna assemblies can be used with standard external units. Deviation in mechanical characteristics of the antenna assemblies results in minor dimensional and strength variations. A way to reduce costs, deviation in geometry and electrical properties, and to scale up production is to manufacture the antenna assemblies as flexible printed circuit boards.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Figure 1:
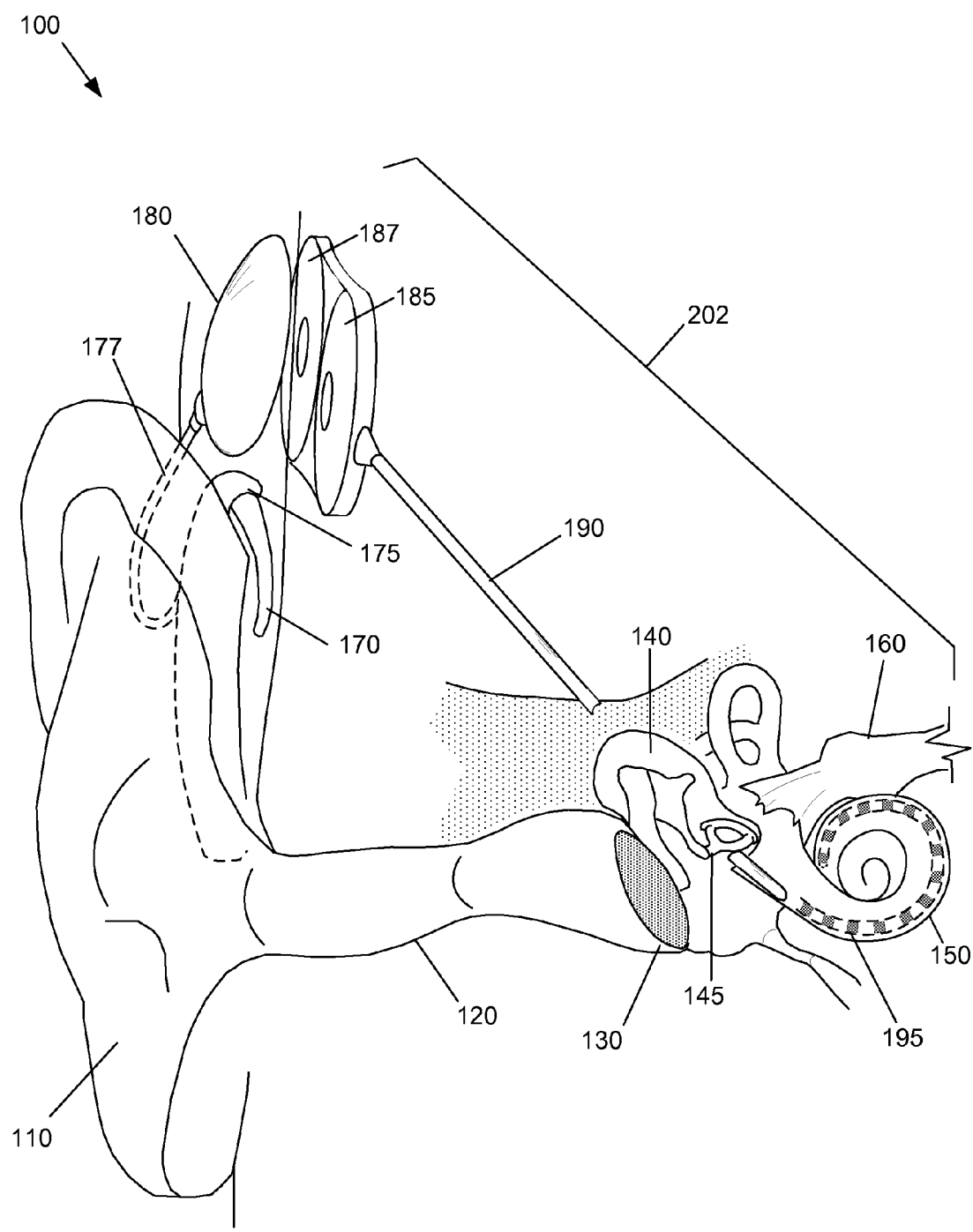
FIG. 1 is a diagram showing an illustrative cochlear implant system in use, according to one example of principles described herein.

FIG. 1 is a diagram showing one illustrative embodiment of a cochlear implant system (100) having a cochlear implant (202) with an electrode array (195) that is surgically placed within the patient's cochlea. Ordinarily, sound enters the external ear, or pinna, (110) and is directed into the auditory canal (120) where the sound wave vibrates the tympanic membrane (130). The motion of the tympanic membrane is amplified and transmitted through the ossicular chain (140), which consists of three bones in the middle ear. The third bone of the ossicular chain (140), the stirrup (145), contacts the outer surface of the cochlea (150) and causes movement of the fluid within the cochlea. Cochlear hair cells respond to the fluid-borne vibration in the cochlea (150) and trigger neural electrical signals that are conducted from the cochlea to the auditory cortex by the auditory nerve (160).

The cochlear implant (202) is a surgically implanted electronic device that provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

Unlike hearing aids, the cochlear implant (202) does not amplify sound, but works by directly stimulating any functioning auditory nerve cells inside the cochlea (150) with electrical impulses representing the ambient acoustic sound. Cochlear prosthesis typically involves the implantation of electrodes into the cochlea. The cochlear implant operates by direct electrical stimulation of the auditory nerve cells, bypassing the defective cochlear hair cells that normally transduce acoustic energy into electrical energy.

External components (200) of the cochlear implant system (100) can include a Behind-The-Ear (BTE) unit (175), which contains the sound processor and has a microphone (170), a cable (177), and a transmitter (180). The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the processor and transmits them to the implanted antenna assembly (187) by electromagnetic transmission. In some cochlear implant systems, the transmitter (180) is held in place by magnetic interaction with a magnet (189) in the underlying antenna assembly (187).

The components of the cochlear implant (202) include an internal processor (185), an antenna assembly (187), and a cochlear lead (190) having an electrode array (195). The internal processor (185) and antenna assembly (187) are secured beneath the user's skin, typically above and behind the pinna (110). The antenna assembly (187) receives signals and power from the transmitter (180). The internal processor (185) receives these signals and performs one or more operations on the signals to generate modified signals. These modified signals are then sent through the cochlear lead (190) to the electrode array (195), which is the portion of the cochlear lead (190) that is implanted within the cochlea (150) and provides electrical stimulation to the auditory nerve (160).

The cochlear implant (202) stimulates different portions of the cochlea (150) according to the frequencies detected by the microphone (170), just as a normal functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

The cochlear lead (190) typically comprises an electrode array (195) that is implanted in one of the cochlear ducts. The electrode array (195) includes several stimulating electrode contacts, conventionally numbering about 6 to 30, longitudinally disposed on a thin, elongated, flexible carrier. The electrode array is pushed into one of the cochlear ducts, such as the scala tympani, to a depth of about 13 to 30 mm via a cochleostomy or a surgical opening made in the round window at the basal end of the duct.

In use, the electrode array (195) delivers electrical current into the fluids and tissues immediately surrounding the individual electrode contacts to create transient potential gradients that, if sufficiently strong, cause the nearby auditory nerve fibers to generate action potentials. The density of electrical current flowing through volume conductors such as tissues and fluids tends to be highest near the electrode contact that is the source of such current. Consequently, stimulation at one contact site tends to selectively activate auditory nerve fibers with spiral ganglion cells that are closest to that contact site.

Figure 2:
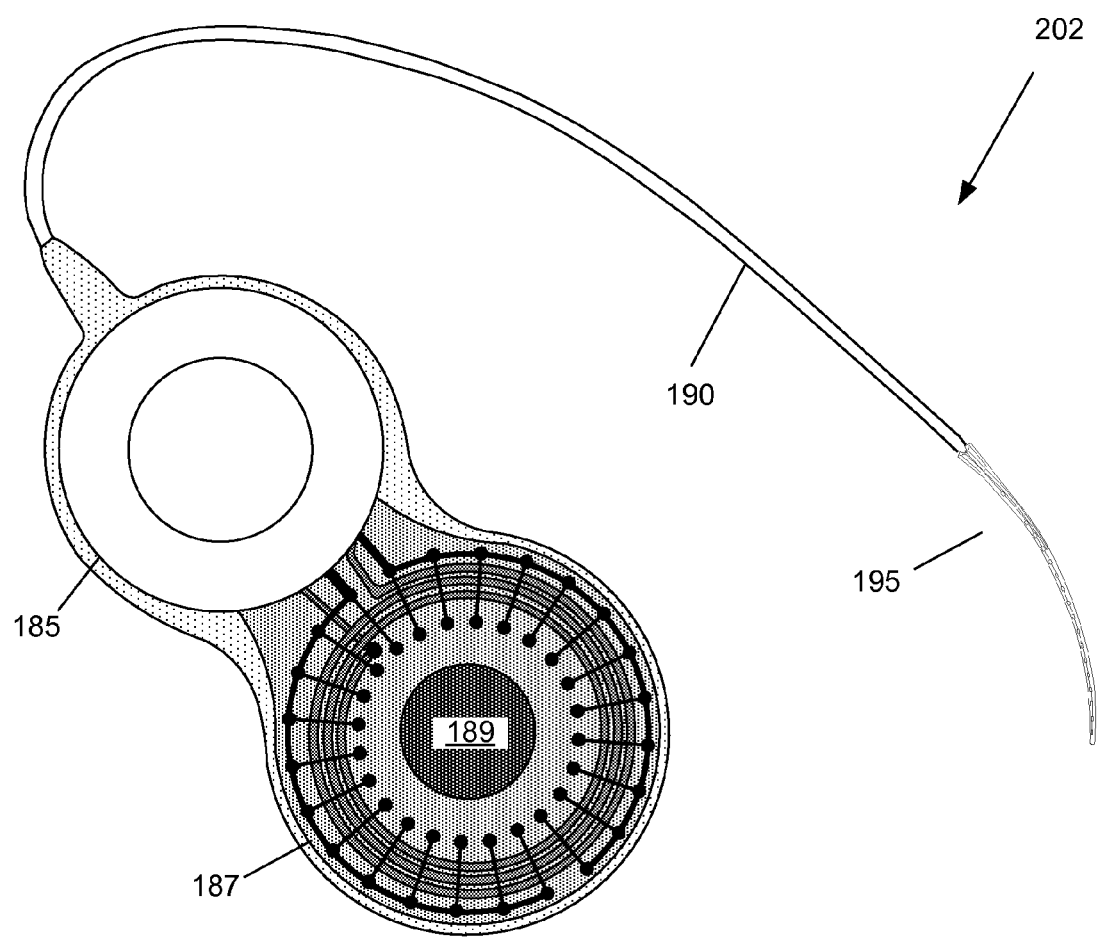
FIG. 2 is a diagram showing the internal components of an illustrative cochlear implant system, according to one example of principles described herein.

FIG. 2 is a diagram showing an illustrative cochlear implant (202) that includes an internal processor (185), an antenna assembly (187), and a cochlear lead (190) with an electrode array (195). The cochlear implant (202) is surgically implanted such that the electrode array (195) is internal to the cochlea, as shown in FIG. 1. As discussed above, the internal processor (185) and antenna assembly (187) are secured beneath the user's skin, typically above and behind the pinna (110), with the cochlear lead (190) connecting the internal processor (185) to the electrode array (195) within the cochlea. A magnet (189) is located in the center of the antenna assembly (187). The magnet (189) holds the external transmitter (180, FIG. 1) in place. The antenna assembly (187) receives signals and power from the transmitter (180, FIG. 1) and sends the signals/power to the internal processor (185). The internal processor (185) modifies the signals and passes them through the cochlear lead (190) to the electrode array (195). The electrode array (195) then electrically stimulates the appropriate portions of the auditory nerve. This provides the user with sensory input that is a representation of external sound waves sensed by the microphone (170, FIG. 1).

Figure 3:
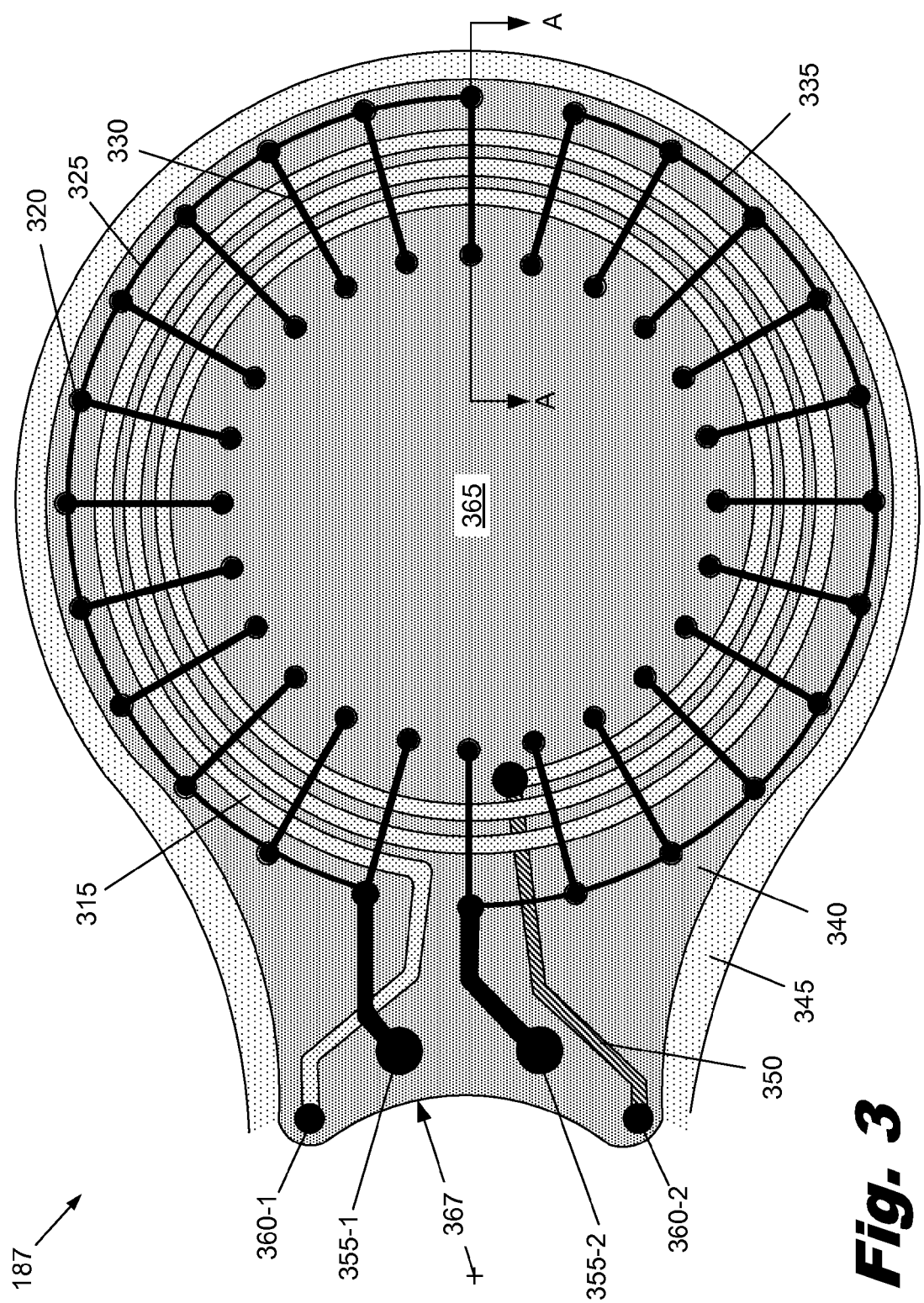
FIG. 3 is a top view of an illustrative implantable antenna assembly, according to one example of principles described herein.

FIG. 3 is a top view of an illustrative implantable antenna assembly (187). In this example, the implantable antenna assembly (187) includes a flexible multilayer substrate (340), a number of conductive metal traces (315, 320, 325, 330, 335, 350) printed on the flexible substrate, and encapsulant (345). In one implementation, the layers of the flexible substrate (340) are made up of thin sheets of polymer. For example, polymers that can be used as flexible substrates include Liquid Crystal Polymer (LCP) or Polyimide (PI).

The conductive metal traces (315, 320, 325, 330, 335, 350) are formed on various surfaces of the flexible substrates to create an inductor (315, 350) and a shield (320, 325, 335). The metal traces may be formed using a variety of techniques including printing, chemical etching and laser machining. The metals that are fused to the polymer sheets to form traces are noble metals such as titanium, platinum, gold or alloys thereof. A first substrate layer includes conductive traces that make up the inductor on one side and one trace to connect the inductor to the implant electronics on the opposite side. Traces formed on the second and third substrate layers form the shield. In one example, the noble metal used to form the traces is gold. To facilitate adhesion of gold to the polymer substrates, a very thin adhesion layer of titanium or platinum can be used. The thickness of the traces is selected to achieve the desired electrical resistance and flexibility. The sheet thicknesses of the substrates are in a range of 0.0005 to 0.002 inches (12.5 to 50 µm). The flexible printed antenna includes a number of connection points (355, 360) that interface with the internal processor (185, FIG. 2). The connection points (355, 360) may be flat pads direct connection to mating pads on the internal processor, plated through holes that connect to posts on the internal processor, or other appropriate configuration.

The traces include a spiral inductor coil (315) that is connected at either end to two of the connection points (360). The inductor coil (315), and the entire antenna assembly, is specifically tuned receive the signals and power from the exterior transmitter (180, FIG. 1). Efficient transmission of these signals and power is particularly important to preserve the battery life of the cochlear implant system. The inductor length, number of turns, width, and thickness are selected to meet the inductance, quality factor (Q), and resistance requirements of the radio frequency electronics.

The shield is made up of two separate segments (325, 335). The segments include conductive traces (330) that surround the antenna coil (315). These conductive traces are connected to two terminals (355). By grounding the two terminals (355), the shield can protect the inductor (315) from undesired noise and alternation of the antenna's properties.

The antenna assembly (187) may include features that allow it to be positioned and interface with the internal processor more easily. In this implementation, a radius (367) is included in near the connection points (355, 360). The radius (367) matches a corresponding curvature on the outer surface of the internal processor (185, FIG. 2). When the radius (367) is brought into contact with the internal processor (185, FIG. 2), it acts as a reference that allows the antenna assembly to be more accurately and easily positioned with respect to the internal processor.

Figure 4:
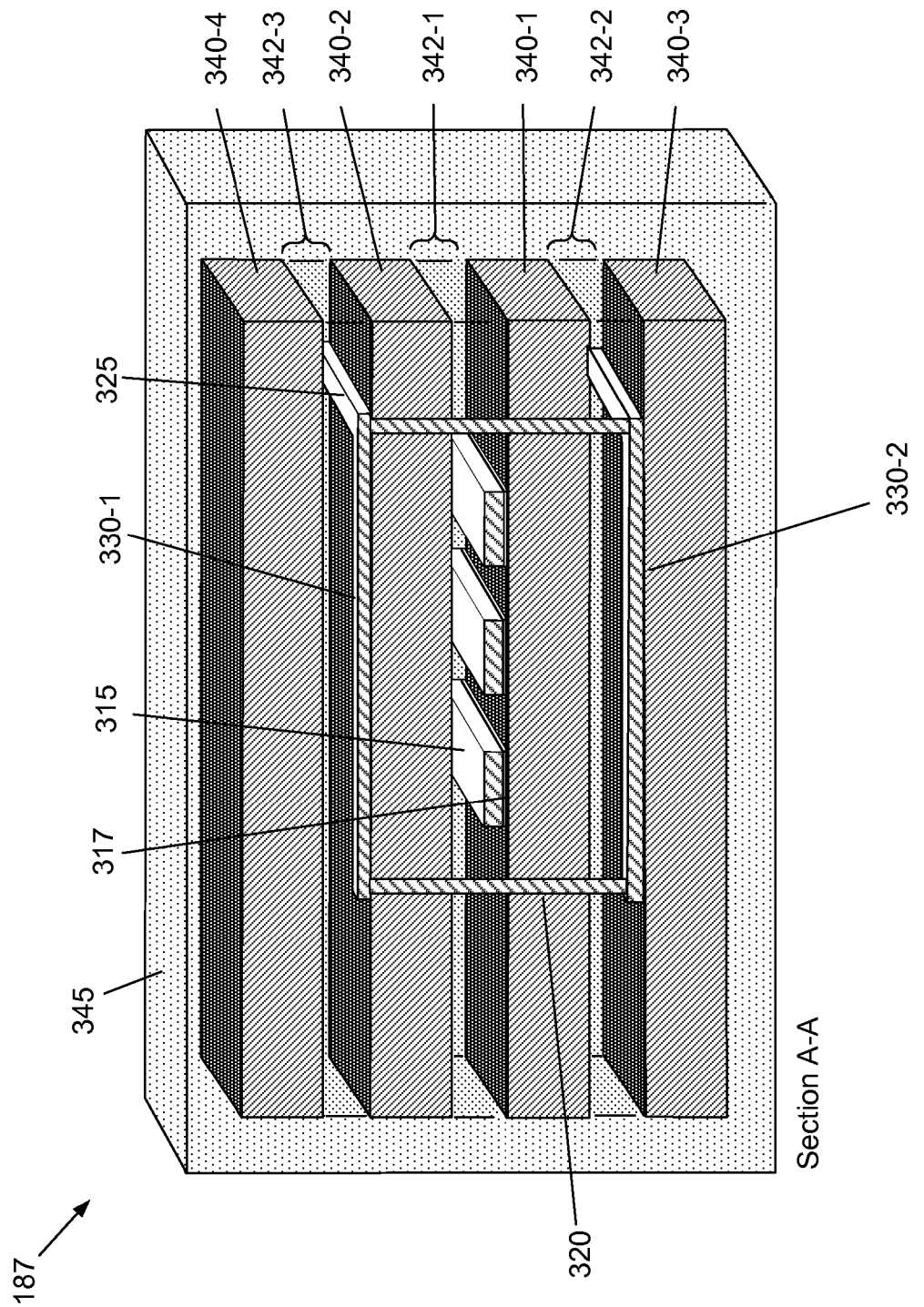
FIG. 4 is a cross sectional diagram of an illustrative implantable antenna assembly, according to one example of principles described herein.

In one example, flexible printed antenna assembly (187) includes four individual substrate layers that are laminated together. FIG. 4 is a cross sectional diagram of the implantable antenna assembly (187) taken along the section line A-A in FIG. 3. In this cross sectional diagram, the substrate layers (340) that make up the antenna assembly are shown, with electrical traces (315, 330 325) deposited on some of the flexible substrates. As discussed above, these flexible substrates may be formed from a variety of flexible biocompatible materials, including polyimide or liquid crystal polymer. Polyimides have superior chemical resistance and excellent mechanical properties, with a tensile strength of 75-90 MPa or greater. In some medical applications, polyimide has displayed a strength of approximately 392 MPa. The individual polyimide substrates may be relatively thin. As discussed above, the polyimide substrates may have thicknesses that are between 0.0005 and 0.002 inches (12.5 to 50 µm). In one example, the polyimide substrates are 0.001 inch (24.5 µm) thick.

In this illustrative implementation the traces in the antenna assembly (187) are formed on the polyimide substrates. The traces include a thin adhesion layer (317). The adhesion layer (317) is made up of a material that strongly binds with both the polyimide and the noble metal deposited over the adhesion layer. For example, the adhesion layer (317) may be titanium or platinum and the traces (315, 325, 330) may be formed from gold or a gold alloy. The adhesion layer and traces may be deposited using a variety of methods including plating, sputtering, vapor deposition or other methods. The traces can be shaped using chemical etching, laser ablation, or other suitable technique.

Traces (315) that make up the antenna inductor are formed on the first flexible substrate (340-1). The inductor traces (315) may have larger cross sections than other traces and be formed from gold or a gold alloy. Gold provides good flexibility and superior electrical conductivity. The shields include gold traces (330) formed on a second substrate (340-2) and third substrate (340-3). These traces (330) are connected together using vias (320) that pass through the first and second substrates (340). When complete, the shields include a number of conductive loops that pass around the traces that make up the inductor. In one implementation, the inductor trace has a thickness of approximately 0.0007 inches (18 µm) and a width of approximately 0.02 inches (500 µm). The shield traces have a thickness of approximately 0.0009 inches (23 µm) and a width of approximately 0.007 inches (179 µm).

After the desired traces are formed on the substrates, the substrates are laminated together using an intermediary adhesive (342). The thickness of the adhesive (342) in FIG. 4 is illustrated as being thinner than the polyimide substrates (340). However, the thickness of the adhesive (342) can be selected to accommodate the traces and to provide the desired level of adhesion between the substrates (340). For example, the thickness of the adhesive may be approximately 0.0008 inches (20 µm).

The design illustrated in FIG. 4 includes an additional outer polyimide (PI) substrate (340-4). This substrate covers the traces on the second substrate (340-2) to protect them from abrasion and handling. When complete, the thickness of the laminated multilayer circuit may be less than 0.030 inches (762 µm). Assuming that there are 4 metal layers with a thickness of about 0.001 inches (24.5 µm), 5 polymer layers with a thickness of about 0.001 inches (24.5 µm), and 4 adhesive layers with a thickness of about 0.001 inches (24.5 µm), the overall thickness of the antenna assembly (187) before encapsulation is approximately 0.013 inches (330 µm) thick. The layers from bottom to top in the cross section shown in FIG. 4 are as follows:

PI/Ti/Au/Adhesive/PI/Ti/Au/Adhesive/PI/Ti/Au/Adhesive/PI.

The thickness of these layers may vary. In general, the unencapsulated antenna assembly (187) may have a thickness between 200 and 400 µm. Encapsulation with 0.008 inch (203 µm) thick layer of silicone results in an encapsulated thickness of approximately 0.029 inches (737 µm). This relatively thin and flexible antenna assembly (187) may have a number of advantages, including being more flexible, easier to implant, less noticeable to the patient, and less prone to damage. The flexibility of the antenna assembly allows it to adapt to the contours of the patients bone structures. The assembly's thinness and flexibility allows it to be surgically positioned with minimal trauma to the patient.

The antenna assembly can be subjected to impact from externally applied forces, such as those associated with the falling of a patient or a blow to the patient's body in the region of the implanted medical device. Such impact forces can cause antennas that are formed from wire to fail from a tensile breakage of wire. By contrast, the present design uses traces that are formed within a multilayer flexible circuit board. The polyimide that makes up the multilayer flexible circuit board is flexible through its thickness but resists in-plane stretching that might result in breakage of the traces. Thus, the antenna can deform rather than break if the impact is normal to the plane of the antenna. The strength of the antenna assembly resists stretching from oblique impacts.

The impact resistance of the antenna assembly was tested repeatedly impacting the antenna assembly using a calibrated surface striker. The impact produced by the surface striker was at a 10 degree angle from a normal vector that is perpendicular to the plane of the antenna assembly. The antenna assembly was placed on a metal surface (to simulate the skull) and a 2.8 mm thick polyurethane sheet was placed over the antenna assembly (to simulate skin covering the antenna assembly). The surface striker repeatedly impacted the antenna assembly with energies of up to 13 joules. There was no damage to the antenna assembly.

Figure 5:
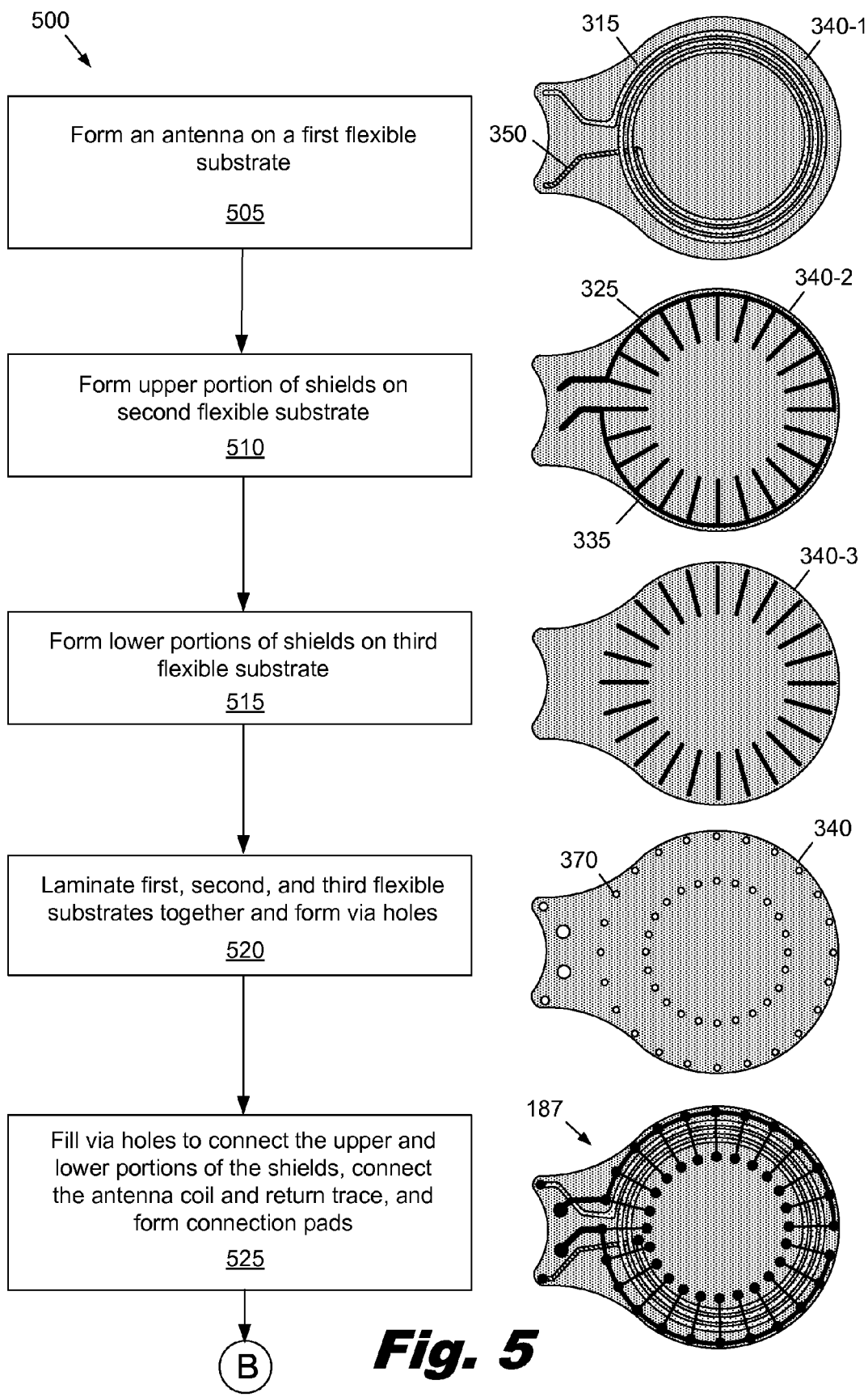
FIG. 5 is a flowchart and accompanying diagrams that show an illustrative method forming an implantable antenna assembly and integrating the antenna assembly into a cochlear implant, according to one example of principles described herein.
Figure 5:
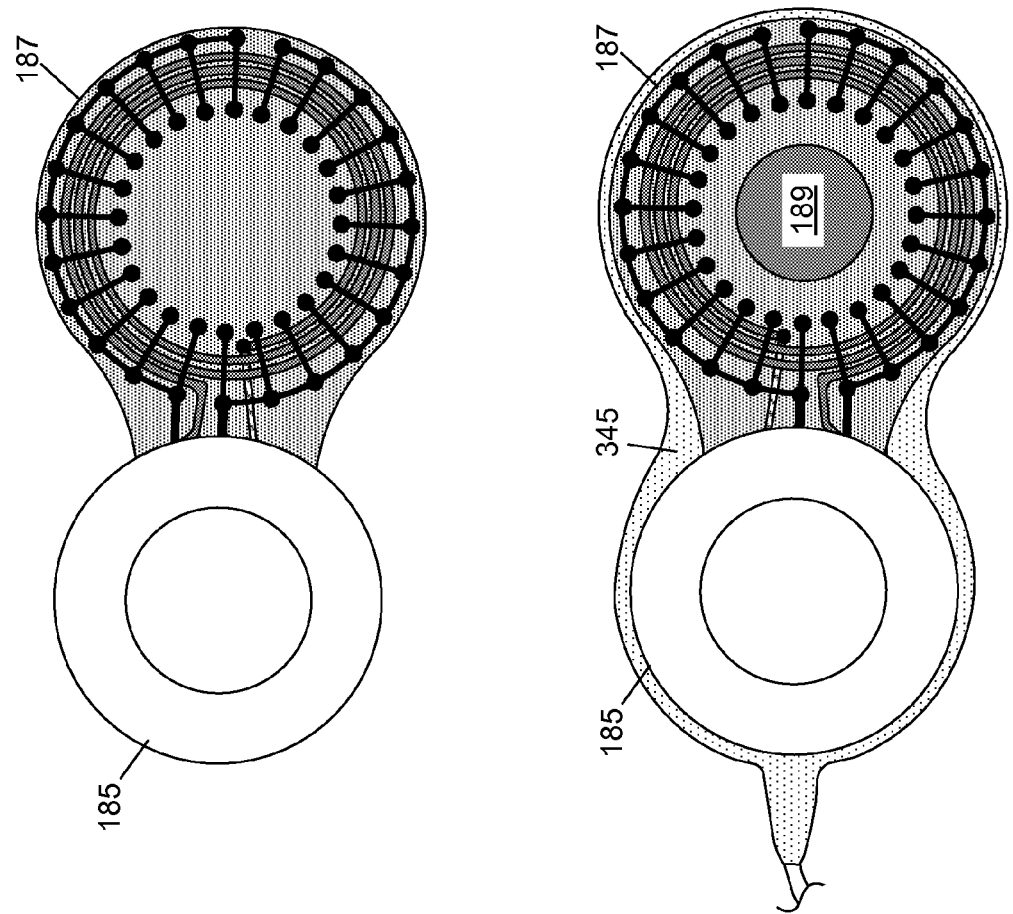
Figure 5:
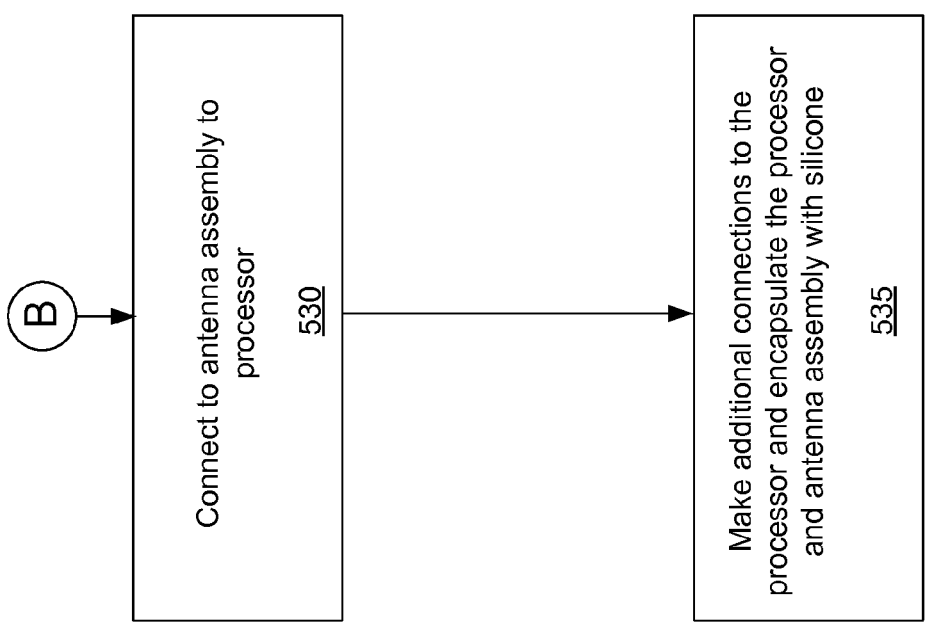

FIG. 5 is a flowchart and accompanying diagrams that show an illustrative method forming an implantable antenna assembly and integrating it into a cochlear implant. An inductor is formed on a first flexible substrate (step 505). In this example, the inductor includes an inductor coil formed from a continuous trace on one side of the first flexible substrate and a return trace (350) formed on the opposite side of the substrate. The return trace (350) is connected to the inductor coil by a via that passes through the thickness of the first flexible substrate. By forming the return trace (350) on the opposite side of the substrate, the return trace can connect the inner circle of inductor coil to the desired location outside of the inductor coil without electrically intersecting any of other portions of the inductor.

Upper portions of the shields are formed on a second flexible substrate (340-2) (step 510). These upper portions are two arcs (325, 335) with inwardly extending traces. An extension is formed from the end of each arc to allow the arcs to be connected to an electrical ground. In this implementation, the electrical ground is the titanium housing of the implanted processor.

Lower portions of the shields are formed on a third flexible substrate (step 515). The lower portions of the shields include a number of radial spokes that extend inward from the outer perimeter of the third flexible substrate toward the center.

In this example, the first, second and third flexible substrates are laminated together and via holes are formed through the substrates (step 520). Although the illustrations show the substrates as having their final rounded shape and the center cutout for the magnet, traces for multiple layers and multiple antennas can be formed on a single sheet of polyimide. This allows for many layers to be formed in a single series of operations. The sheet can then be cut into the individual substrates and stacked together to form the multilayer flexible circuit. In other embodiments, the multiple sheets may be laminated together and then cut into individual assemblies.

The via holes may be formed in a variety of ways, including using laser machining, mechanical punching, drilling or other appropriate technique. In some examples, the via holes may be formed through individual substrates prior to lamination. For example, the first substrate uses a via to connect the return trace to the antenna coil. This via only needs to pass through the first substrate. However, forming this via in the just the first substrate can require several separate operations. In other examples, all the vias are formed simultaneously and pass all the way through the three stacked substrates. For example, the via holes may be formed at the same time the laminated substrates are cut into individual assemblies.

The via holes are filled with a noble metal. This forms vias that connect to traces that intersect the via holes. The vias connect the upper and lower portions of the shields, connect the antenna coil and the return trace, and form connection points. As discussed above, the connection points may be formed by plating the via holes and leaving a through aperture sized to receive posts on the internal processor. For example, the interior of via holes that are designed to form connection points may be plated to a minimum thickness with a noble metal. In one embodiment, the minimum thickness is 0.001 inches (25 µm).

Additional layers may be laminated over the top and/or bottom of the three laminated substrates. These layers can serve to protect the traces from mechanical abrasion and to further isolate the traces from the implanted environment. In some examples, the additional layers may be formed from the same material as the flexible substrates. If present, the additional layers do not cover the connection points.

Following the lamination of the additional layers, if any, the antenna assembly is complete and can be connected to the processor (step 530). The antenna assembly can be connected to the processor by electrically connecting the connection points to contacts on the processor (185). To connect the coil to the implants electronics, four holes have been drilled through the entire structure that conform to the geometry of the feedthrough pins on the implants case. The connection of the inductor and shield to the case can be made in a variety of ways including conductive epoxy.

Additionally or alternatively, some of the connection points may be flat pads. These pads on the antenna coil can be electrically connected to corresponding pads on a hermetic electrical feedthrough. In some embodiments, this hermetic electrical feedthrough is disposed on the bottom of the processor. The pads on the antenna assembly can be connected to the processor using a number of techniques including laser welding and soldering. Connecting the pads to the processor electrically and mechanically connects the antenna assembly to the processor.

Additional connections can be made to the processor and the processor and antenna assembly can be encapsulated (step 535). The additional connections may include connecting the electrode array to the processor. These additional connections may be formed before or after the antenna is connected to the processor. The encapsulant may be medical grade silicone. Silicone is flexible and biocompatible and acts as a cushion between the surrounding biological tissues and the implanted components. The silicone may also act as a strain relief that mechanically joins the various components and prevents kinking of electrical conductors. In some embodiments, the silicone overmold (345) includes a pocket over the center of the antenna (187) that retains the magnet (189).

The implementation given above is only one example. A variety of other methods could be used, including methods that add, combine, omit, or reorder steps. For example, the return trace could be formed on the third substrate with the lower portions of the shields. This would eliminate patterning of the back surface of the first substrate.

Although the description above describes a printing process being used to form the traces on the various substrate surfaces, other techniques could also be used. For example, the traces could be formed from sheets of conductive foil that are then adhered to and sandwiched between substrate layers. The sheets of conductive foil could be platinum or gold foil that is cut to shape using laser or micro-machining.

Figure 6A:
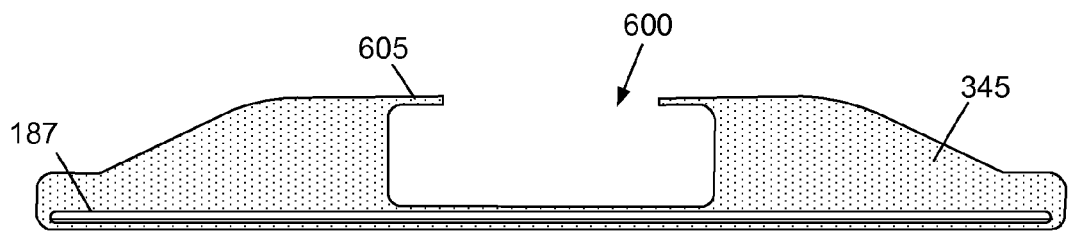
FIGS. 6A-6D are cross sectional views of an antenna assembly with a pocket to retain a magnet, according to one example of principles described herein.
Figure 6B:
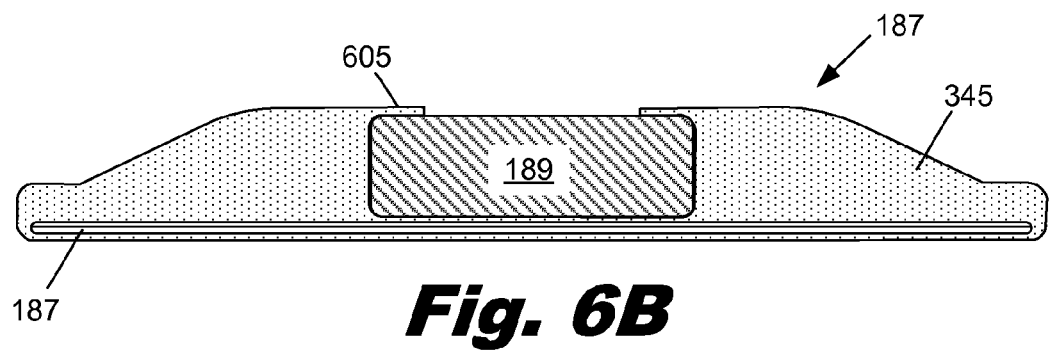

FIGS. 6A-9C show a number of illustrative ways to retain the magnet (189) in a desired location relative to the antenna assembly (187). FIG. 6A a cross sectional view of the antenna assembly (187) and the encapsulant (345) with a pocket (600) to retain magnet (189). In this example, the pocket (600) includes a cavity with sized to receive the magnet (189) and a lip (605) that extends around the aperture of the pocket (600). FIG. 6B shows the magnet (189) positioned within the cavity, with the lip (605) retaining the magnet (189) in the encapsulant (345) and in the correct position over the antenna assembly (187). To minimize the size of the magnet (189), very strong permanent magnet material, such as neodymium alloys are used. The neodymium magnet material is shaped, magnetized and encased in a hermetic titanium case to form the magnet (189). FIG. 6C shows the antenna (187) implanted in a patient, with the bottom of the encapsulant against the skull (615) and soft tissues (610), including skin, over the top of the antenna assembly (187).

Figure 6C:
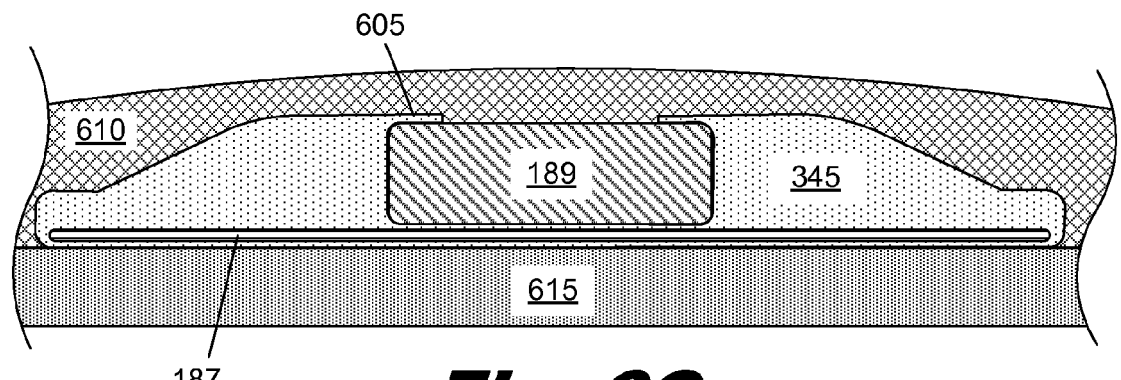

One consideration in the design of a cochlear implant is the ability to remove any magnetic material that may adversely affect diagnostic imaging required by the patient. Diagnostic imaging that may be adversely affected by the magnet includes magnetic resonance imaging (MRI) and computed tomography (CT) scans. An MRI uses a powerful magnetic field to align polar molecules in the human body. Perturbations of this alignment are used to make two and three dimensional images of soft tissues in the body. An MRI may be particularly useful for imaging the brain, muscles, heart and cancers. However, the application of the magnetic field during an MRI interacts with the magnet (189) to produce undesirable forces and possibly motion of the magnet and/or cochlear implant. A CT scan uses X-rays to image structures in the body. The magnet can disrupt the imaging produced by the CT scan in areas that are close to the magnet. This can be particularly undesirable when the area of interest is close to the magnet and cochlear implant. Consequently, one of the considerations in designing a cochlear implant is to allow a surgeon to easily remove the magnet (189) prior to diagnostic imaging and then replace the magnet following the diagnostic imaging. In FIG. 6C, the magnet is easily accessible. To remove the magnet (189), the surgeon makes an opening in the soft tissues (610), pushes back the lip (605), and extracts the magnet (189). To replace the magnet (189) the surgeon simply reverses the operation.

Figure 6D:
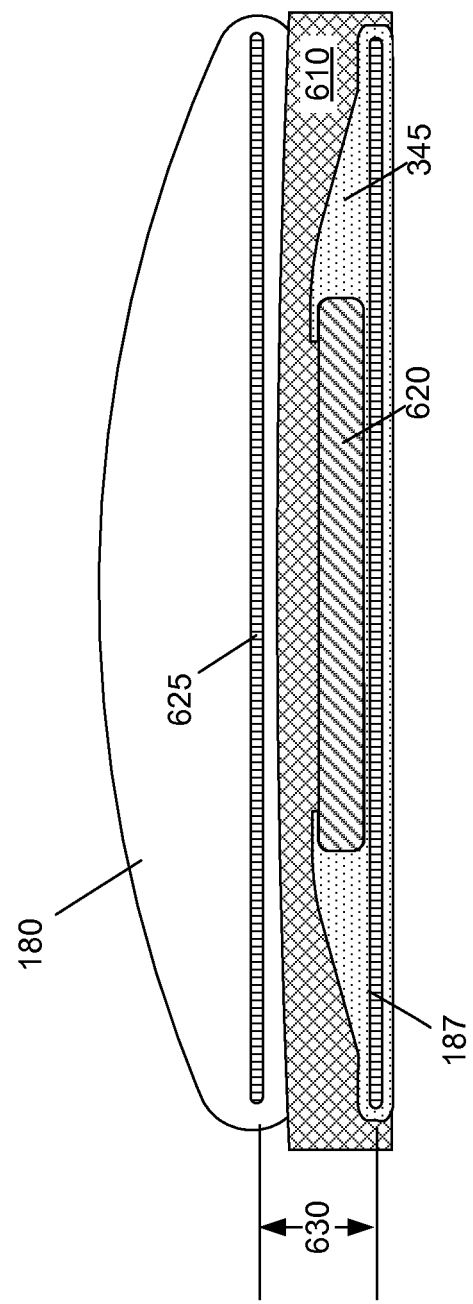

In an illustrative embodiment shown in FIG. 6D, a significantly thinner magnet (620) can be used. The thinner magnet (620) has a larger diameter than the magnet (189) shown in FIGS. 6B and 6C. For example, the thinner magnet may have a thickness of 2 to 3 millimeters. FIG. 6D shows the antenna assembly implanted under soft tissue (610) with the headpiece (180) magnetically held in place over the antenna assembly. The distance (630) between the inductor coil in the antenna assembly (187) and the transmission coil (625) in the head piece (180) can significantly influence the transmission efficiency of electrical power to the implanted portion of the cochlear implant. In general, a smaller distance (630) allows for a higher transmission efficiency between the two coils. By using a thinner magnet (620), the distance (630) between the coils is reduced. Additionally, the implant is less noticeable to the patient because it protrudes less.

Figure 7A:
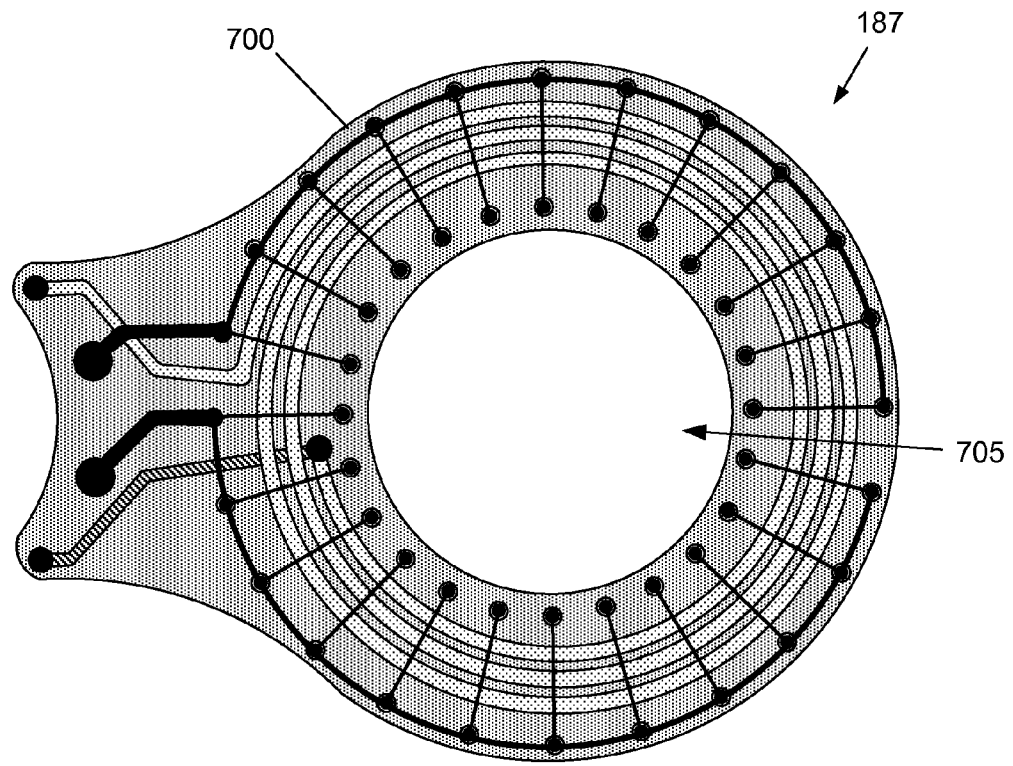
FIGS. 7A-7C and 8 are diagrams of an antenna assembly with a central aperture, according to one example of principles described herein.
Figure 7B:
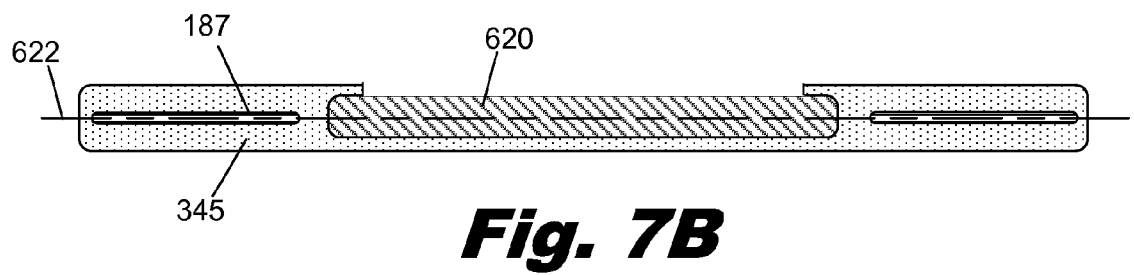
Figure 7C:
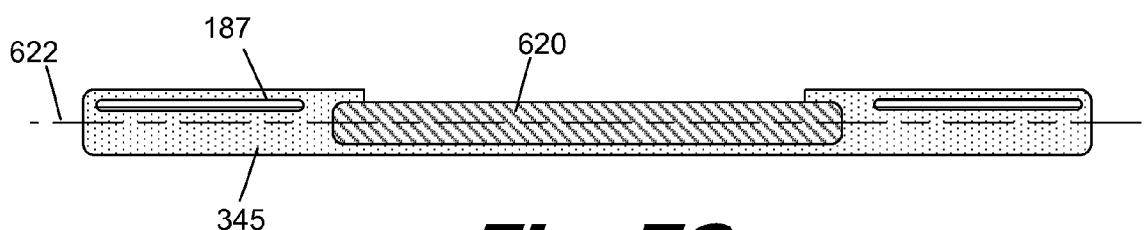

FIG. 7A describes an illustrative embodiment where a central aperture (705) is formed in the antenna assembly (187). The central aperture may be formed in a variety of ways, including punching and laser machining. In general, it is desirable that the cut that forms the central aperture is smooth and uniform to avoid roughness that may produce stress concentrations when the antenna assembly is subject to stress. In this example, the central aperture (705) has a diameter that is larger than the diameter of the magnet. This allows the magnet to fit into the aperture (705). The antenna inductor coil can then be moved even closer to the soft tissue and the transmission coil in the head piece by appropriately positioning the magnet in the aperture. FIG. 7B shows the magnet positioned in the aperture so that the centerline of the magnet is in the same plane as the antenna assembly (187). FIG. 7C shows the magnet (620) positioned in the aperture so that the antenna assembly (187) is located above the magnet (620). This configuration moves the antenna assembly (187) very close to the skin and minimizes the distance between the transmission and antenna coils. In both FIG. 7B and 7C, a pocket is formed in the encapsulant to retain the magnet. The encapsulant is also used to form a relatively flat compliant bottom surface that rests against the patient skull.

Figure 8:
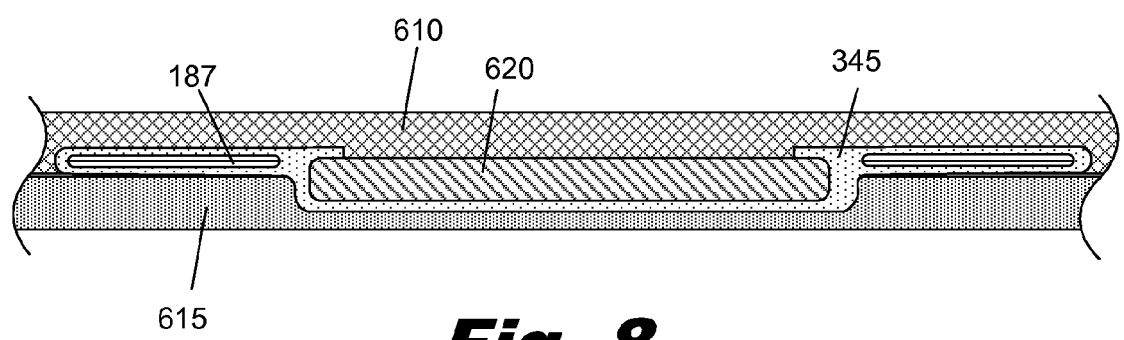

The antenna configurations shown above are only illustrative examples of principles described herein. A variety of other configurations could be used. FIG. 8 shows an embodiment that is similar to the embodiment shown in FIG. 7C. However, in this implementation an indentation has been surgically formed in the patient's skull (615) to accommodate the magnet (620) extending below the antenna assembly (187). In this example, the cochlear implant lifts the overlying skin by the thickness of the antenna assembly (187) and the encapsulant (345). As discussed above, the antenna assembly (187) can be very thin. In some embodiments, the protrusion of the skin caused by the assembly shown in FIG. 8 may be almost unnoticeable.

Figure 9C:
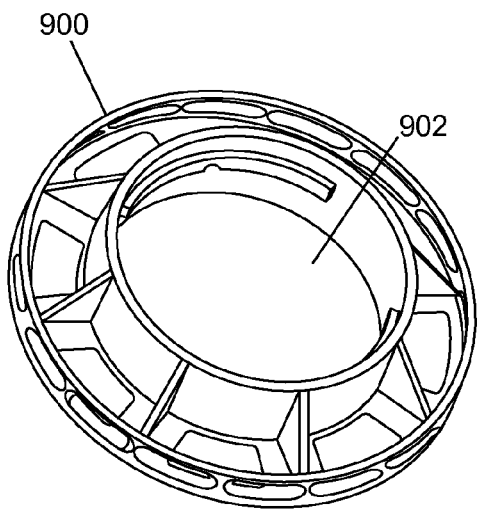
Figure 9C:
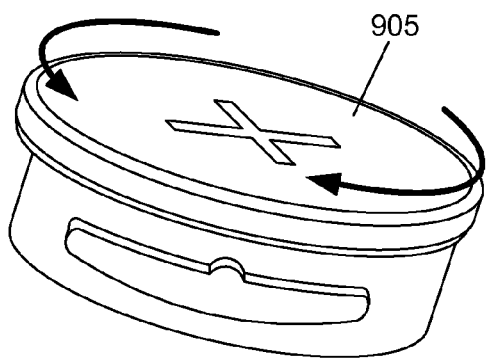
Figure 9C:
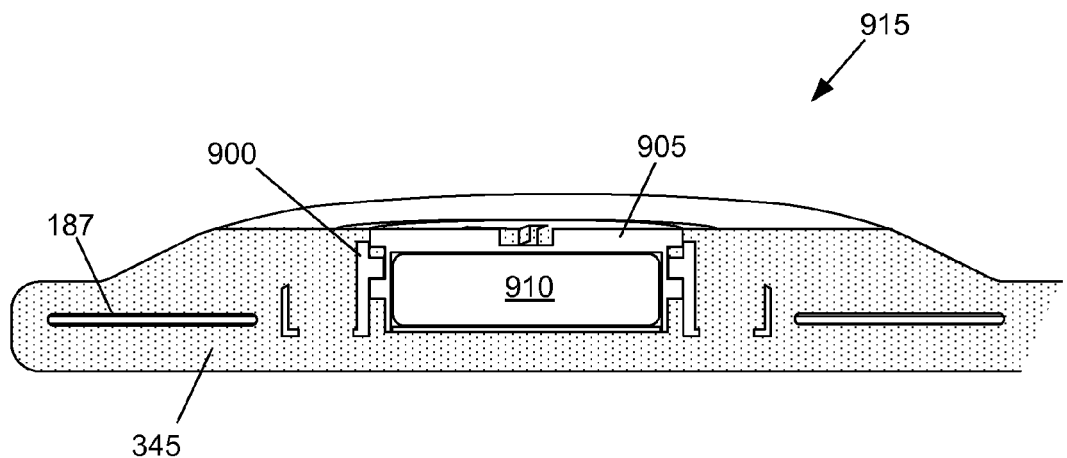

All of the embodiments described above allow for the separate explanation of the magnet without disrupting the other components of the cochlear implant. The magnet is directly accessible after creating an opening in the overlying skin. The magnet is removed by pushing back the encapsulant lip around the opening of the pocket and lifting the magnet out of the pocket. FIGS. 9A-9C show an alternative method for magnet retention. This method uses a nest or cage (900) that provides additional structure to retain the magnet (905). In this example, the magnet (905) is locked into the cage (900) by inserting it into a central aperture (902) of the cage and rotating the magnet (905). In some circumstances, the cage (900) may retain the magnet (905) sufficiently to prevent the magnet from shifting or becoming dislodged during an MRI procedure. This can eliminate the need for the magnet to be removed. However, if the surgeon determines that it is best for the magnet to be removed, magnet (905) can be easily disengaged using a tool to rotate the magnet and lift it from the central aperture (902).

FIG. 9C shows a cross section of the cage (900), magnet (910), flexible antenna assembly (187), and encapsulant (345). In some embodiments, the cage (900) may be directly connected to the flexible antenna assembly (187). In the embodiment shown in FIG. 9A-9C, the cage (900) contains features designed to engage with encapsulant (345) and minimize motion of the cage (900) with respect to the encapsulant (345) and antenna assembly (187). The antenna assembly (187) may be located in a variety of positions with respect to the cage (900), with positions that are closer to the skin providing greater energy transmission efficiency. The cage (900) may also be recessed into an indentation formed in the skull as described above with respect to FIG. 8.

The principles described above can be used to create antenna assemblies that are flexible and implantable. The use of printing techniques on a multilayer substrate results in an antenna assembly that can be produced with low cost and with low electrical and mechanical deviation. The ability to repeatably produce an antenna design with low electrical deviations can increase the efficiency of the energy transfer to the antenna and extend the battery life of the exterior device. Additionally, the multilayer antenna assembly is an extremely thin, strong design. This increases the safety of the antenna assembly and makes it less intrusive when implanted.

The preceding description has been presented only to illustrate and describe examples of the principles described. This description is not intended to be exhaustive or to limit these principles to any precise form disclosed. Many modifications and variations are possible in light of the above teaching.

What is claimed is:

1. An implantable antenna assembly comprising:
a multilayer flexible printed circuit board comprising a first flexible substrate, second flexible substrate, and third flexible substrate;
an inductor comprising electrically conductive traces disposed on the first flexible substrate; and
a shield comprising electrically conductive traces disposed on the second flexible substrate and third flexible substrate, the shield surrounding the inductor.

2. The assembly of claim 1, in which the electrically conductive traces comprise a noble metal disposed over a metal adhesion layer.

3. The assembly of claim 2, in which the noble metal comprises at least one of: gold, a gold alloy, platinum, and a platinum alloy.

4. The assembly of claim 3, in which the electrically conductive traces disposed on the first flexible substrate and electrically conductive traces disposed on the second and third flexible substrates comprise gold.

5. The assembly of claim 2, in which the metallic adhesion layer comprises at least one of titanium and platinum.

6. The assembly of claim 1, further comprising vias passing through the flexible substrates, the vias electrically connecting traces formed on different ones of the flexible substrates.

7. The assembly of claim 1, in which the flexible substrates comprise an organic polymer.

8. The assembly of claim 7, in which the flexible substrates comprise polyimide.

9. The assembly of claim 1, further comprising an encapsulant, the encapsulant encapsulating the antenna assembly.

10. The assembly of claim 9, in which the encapsulant comprises silicone.

11. The assembly of claim 9, further comprising a pocket for retaining a magnet, the pocket formed in the encapsulant.

12. The assembly of claim 11, further comprising an aperture in the flexible substrates, the aperture having a diameter larger than the magnet, in which the pocket is formed in the aperture such that the magnet, when placed in the pocket extends through the aperture.

13. The assembly of claim 1, in which the shield extends around the inductor.

14. The assembly of claim 1, further comprising adhesive disposed between the flexible substrates, the adhesive binding the flexible substrates together.

15. The assembly of claim 14, in which the implantable antenna assembly before encapsulation has a thickness of less than 400 μm.

16. The assembly of claim 1, in which the first flexible substrate is sandwiched between the second flexible substrate and third flexible substrate.

17. A cochlear implant comprising:
a processor;
an implantable antenna assembly electrically connected to the processor, the implantable antenna assembly comprising:
a multilayer flexible substrate; and
noble metal traces disposed on the multilayer flexible substrate; and
an encapsulant encapsulating the processor and implantable antenna assembly, wherein the encapsulant includes a pocket in which is removably contained a magnet, the magnet being removable from the implant without damage to the implant.

18. A method for forming an implantable antenna assembly comprises:
forming an inductor on a first flexible substrate;
forming a shield on at least one additional flexible substrate;
laminating the flexible substrates together;
forming vias between the substrates to complete electrical paths through the inductor and shield to form the antenna assembly;
attaching the antenna assembly to electronics;
encapsulating the antenna assembly; and
forming a pocket in an encapsulant when the antenna is encapsulated; and
placing a magnet in the pocket, wherein the magnet is removable from the pocket and replacable in the pocket without damage to the encapsulant.

19. The method of claim 18, in which forming the inductor comprises:
forming an inductor coil on the first side of the first flexible substrate; and
forming a return trace on the second side of the first flexible substrate.

20. The method of claim 18, in which forming shield comprises:
forming an upper portion of the shield on a second flexible substrate; and forming a lower portion of the shield on a third flexible substrate.

21. The method of claim 18, in which forming the inductor and shield comprises:
depositing an adhesion metal on the substrates;
depositing a noble metal on the adhesion metal; and
etching away portions of the noble metal and adhesion metal to form traces of the inductor and shield.

22. The method of claim 18, in which laminating the flexible substrates together comprises stacking the flexible substrates with the first flexible substrate sandwiched between the second and third flexible substrates.

23. The method of claim 22, in which laminating the flexible substrates together further comprises:
depositing adhesive between the stacked flexible substrates; and
curing the adhesive.

24. The method of claim 23, in which curing the adhesive comprises applying pressure and heat to the stacked flexible substrates.

25. The method of claim 18, in which forming vias comprises:
forming holes through the flexible substrates; and
filling the holes with conductive material.

26. The method of claim 18, in which encapsulating the antenna assembly comprises encapsulating the antenna assembly and electronics with silicone.

27. The method of claim 18, further comprising forming an aperture in the antenna assembly with a diameter greater than the diameter of the magnet, in which the pocket is formed such that when a magnet placed in the pocket, at least a portion of the magnet is within the aperture.

* * * * *